United States Patent
Rich

(10) Patent No.: US 7,121,134 B2
(45) Date of Patent: Oct. 17, 2006

(54) INTEGRATED SAMPLE CELL AND FILTER AND SYSTEM USING SAME

(75) Inventor: David R Rich, Glastonbury, CT (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 10/678,692

(22) Filed: Oct. 3, 2003

(65) Prior Publication Data

US 2004/0065141 A1    Apr. 8, 2004

Related U.S. Application Data

(60) Provisional application No. 60/416,874, filed on Oct. 8, 2002.

(51) Int. Cl.
*G01N 7/00* (2006.01)

(52) U.S. Cl. .................................. 73/23.2; 73/31.07

(58) Field of Classification Search .............. 73/31.07, 73/23.2, 31.05
See application file for complete search history.

(56) References Cited

U.S. PATENT DOCUMENTS

| | | | | |
|---|---|---|---|---|
| 4,268,279 A | * | 5/1981 | Shindo et al. | 95/46 |
| 4,914,720 A | * | 4/1990 | Knodle et al. | 250/343 |
| 4,940,541 A | * | 7/1990 | Aoyagi | 210/321.8 |
| 5,047,627 A | * | 9/1991 | Yim et al. | 250/227.23 |
| 5,192,320 A | * | 3/1993 | Anazawa et al. | 623/23.65 |
| 5,221,474 A | * | 6/1993 | Yokono et al. | 210/436 |
| 5,657,750 A | | 8/1997 | Colman et al. | |
| 2002/0026822 A1 | * | 3/2002 | Reading et al. | 73/31.05 |

* cited by examiner

*Primary Examiner*—Hezron Williams
*Assistant Examiner*—Rodney Frank
(74) *Attorney, Agent, or Firm*—Michael W. Haas

(57) ABSTRACT

Sidestream gas sampling assembly that does not substantially degrade the waveform of expired gases. The gas sampling assembly includes a sample cell portion integrated with a filter portion for separating undesired liquid condensate from respiratory gases to be monitored. The gas sampling assembly is configured to receive expired gases through a gas sampling line, filter undesired liquid condensate from the expired gases through hydrophobic fiber elements and communicate the filtered gases to a sample chamber which is in close proximity to the filter where measurements may be taken thereof e.g., optical or infrared sensing mechanisms. The gases that are substantially free of liquid condensate are then exhausted from the sample chamber.

23 Claims, 4 Drawing Sheets

INTEGRATED SAMPLE CELL AND FILTER AND SYSTEM USING SAME

CROSS-REFERENCE TO RELATED APPLICATIONS

This application claims priority under 35 U.S.C. § 119(e) from provisional U.S. patent application No. 60/416,874 filed Oct. 8, 2002 the contents of which are incorporated herein by reference.

BACKGROUND OF THE INVENTION

1. Field of the Invention

The present invention relates generally to a gas monitoring system, and, in particular, to an integrated sample cell and filter for use in a sidestream gas monitoring system, such filter for separating undesired liquid components from respiratory gases to be monitored in the sample cell.

2. Description of the Related Art

During medical treatment, it is often desirable to monitor and analyze a patient's exhalations to determine the gaseous composition of the exhalate. For instance, monitoring the carbon dioxide ($CO_2$) content of a patient's exhalations is often desirable. Typically, the carbon dioxide (or other gaseous) content of a patient's exhalation is monitored by transferring a portion, or sample, of the patient's expired gases to a suitable sensing mechanism and monitoring system.

Monitoring of exhaled gases may be accomplished utilizing either mainstream or sidestream monitoring systems. In a mainstream monitoring system, the gaseous content of a patient's exhalations is measured in-situ in the patient circuit or conduit coupled to the patient's airway. In a sidestream monitoring system, on the other hand, the gas sample is transported from the patient circuit through a gas sampling line to a sensing mechanism located some distance from the main patient circuit for monitoring. As a patient's expired gases are typically fully saturated with water vapor at about 35° C., a natural consequence of the gas transport is condensation of the moisture present in the warm, moist, expired gases.

Accurate analysis of the gaseous composition of a patient's exhalation is dependent upon a number of factors including collection of a gaseous sample that is substantially free of liquid condensate, which might distort the results of the analysis. As an expired gas sample cools during transport through the gas sampling line to the sensing mechanism in a sidestream monitoring system, the water vapor contained in the sample may condense into liquid or condensate. The liquid or condensate, if permitted to reach the sensing mechanism, can have a detrimental effect on the functioning thereof and may lead to inaccurate monitoring results. Condensed liquid in the gas sampling line may also contaminate subsequent expired gas samples by being re-entrained into such subsequent samples.

In addition to the condensate, it is not uncommon to have other undesirable liquids, such as blood, mucus, medications, and the like, contained in the expired gas sample. Each of these liquids, if present in the gas sample to be monitored, may render analytical results that do not accurately reflect the patient's medical status.

There are numerous ways in which to separate undesired liquids from the patient's expired gas stream to protect the sensing mechanism. For instance, it is known place a moisture trap between the patient and the sensing mechanism to separate moisture from the exhalation gas before it enters the sensing mechanism. The challenge, however, is to achieve the separation without affecting the characteristics of the parameters being measured, e.g., the waveform of the gas to be monitored.

By way of example, carbon dioxide ($CO_2$) is effectively present only in the patient's expired gases. Therefore, the $CO_2$ in an exhaled gas sample, transported through a gas sampling line to the sensing mechanism, fluctuates according to the $CO_2$ present at the point at which the sample is taken. Of course the $CO_2$ level also varies with the patient respiratory cycle. Disturbance to this fluctuation, i.e., decreases in the fidelity of the $CO_2$ waveform, are undesirable, because such disturbances can affect the accuracy of the $CO_2$ measurement and the graphical display of the waveform. For this reason, removal of liquids from the exhaled gas sample is desirably accomplished in such a way that it does not substantially degrade the fidelity of the $CO_2$ waveform. Unfortunately, conventional moisture traps often disturb the waveform to a substantial degree.

Various other techniques have been employed to filter the expired gas stream of the undesired condensate while attempting to permit the waveform to be transported undisturbed. Such techniques include absorbents, centrifugal filters, desiccants, hydrophobic membranes and hydrophilic membranes. One well-established application which has shown some success is the use of hydrophobic hollow fibers as a filter for fluid separation. However, this application often-times still results in degradation of the waveform to some degree due to the physical requirements of the interface between the hollow fibers and the sensing mechanism.

Furthermore, a prominent existing application of hydrophobic hollow fibers as a filter provides a disposable gas sample collection unit that connects to a reusable sensing mechanism. It this conventional filter arrangement, the gas sample collection unit, i.e., the sample cell, is physically located some distance from the filter. The gas passing through the filter is transported to the sample cell via a relatively long tube.

The present inventor recognized that the conventional technique of gathering and transporting the filtered gas sample to a remote sensing mechanism degrades the $CO_2$ waveform measured at the sample cell. More specifically, the present inventor recognized that by locating the filter element some distance from the sample cell and causing the filtered gas to pass through a relatively long conduit to get from the filter to the sample cell, this arrangement effectively dampens the fidelity of the $CO_2$ waveform, for example, by dulling the rising and falling edges of the waveform. Accordingly, a gas sampling assembly that effectively and efficiently separates moisture from a gas sample and that does not substantially degrade the waveform of expired gases measured at the sample would be advantageous.

BRIEF SUMMARY OF THE INVENTION

Accordingly, it is an object of the present invention to provide a gas sampling assembly that overcomes the shortcomings of conventional assemblies. This object is achieved according to one embodiment of the present invention by providing a gas sampling assembly that does not substantially degrade the waveform of expired gases, while separating undesired liquid condensate and other contaminants from the respiratory gases to be monitored.

In a first embodiment, the gas sampling assembly of the present invention includes a filter portion having a housing and a sample collection portion including a body section having a sample chamber defined therein. A first upstream end of the housing is coupled in a gas-tight and fluid-tight arrangement to a gas sampling line through which a gas sample to be monitored may be received. A second downstream end of the housing is coupled in a gas-tight and fluid-tight arrangement to the body section of the sample collection portion. A termination block is provided in a first side portion of the body section. A second side portion of the body section includes a conduit defined therein through which a filtered gas sample is exhausted from the sample chamber. Disposed within the housing of the filter portion is one or more substantially hydrophobic fiber elements. Each hollow fiber element includes an upstream closed end and a downstream open end, each upstream closed end being positioned near the first upstream end of the filter portion. In a preferred embodiment, the fiber element are hollow to readily conduct gas passing through the wall of the fiber to the open, downstream end.

In one embodiment of the present invention, the downstream portions of the hollow fiber elements, i.e., the open ends thereof, are embedded in the termination block such that the open ends of the hollow fiber elements extend beyond the termination block and directly into the sample chamber. In another embodiment, the ends of the fiber elements do not extend beyond the termination block.

In use, a gas sample enters the housing in the filter portion of the gas sampling assembly through the gas sampling line. As the gas sample enters the filter portion, it encounters the closed ends of the hollow fiber elements. Because the hollow fiber elements are formed of a hydrophobic material, gases are permitted to pass therethrough but liquids are preventing from passing through the fiber elements. In a preferred embodiment, the hollow fibers are microporous to provide the filtering property. Moreover, because the termination block forms a gas-tight and fluid-tight seal across the inner perimeter of the first side portion of the sample collection portion, and a fluid-tight and gas-tight seal is also formed between the second downsteam end of the filter portion and the sample collection portion, gases that are substantially free of liquid condensate are permitted to pass only through the hollow fiber elements and into the sample chamber. On the other hand, any liquid present in the expired gases is substantially prevented from leaving the filter portion of the gas sampling assembly. Instead, liquids collect within a fiber chamber within the housing of the filter portion.

The gases substantially free of liquid condensate and contaminants pass through the hollow fiber elements and are collected in the sample chamber where desired measurements may be taken thereof, e.g., using optical sensing techniques and the like. The gas is then exhausted through the conduit formed in the second side portion of the sample collection portion. In this manner, liquids are substantially prevented from reaching the sample chamber. Accordingly, measurements taken of the gases in the sample chamber are less likely to be distorted due to moisture or other contaminants in the gas sample.

In one embodiment of the present invention, the open ends of the hollow fiber elements are situated such that gas existing the interior of the fibers is disposed directly into the sample chamber. As a result, the waveform of the exhaled gas sample is permitted to proceed substantially undisturbed from the point at which the sample is collected to the point at which measurements are taken.

The present invention also pertains to sidestream gas monitoring system that includes the above-described gas sampling assembly embodiments.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
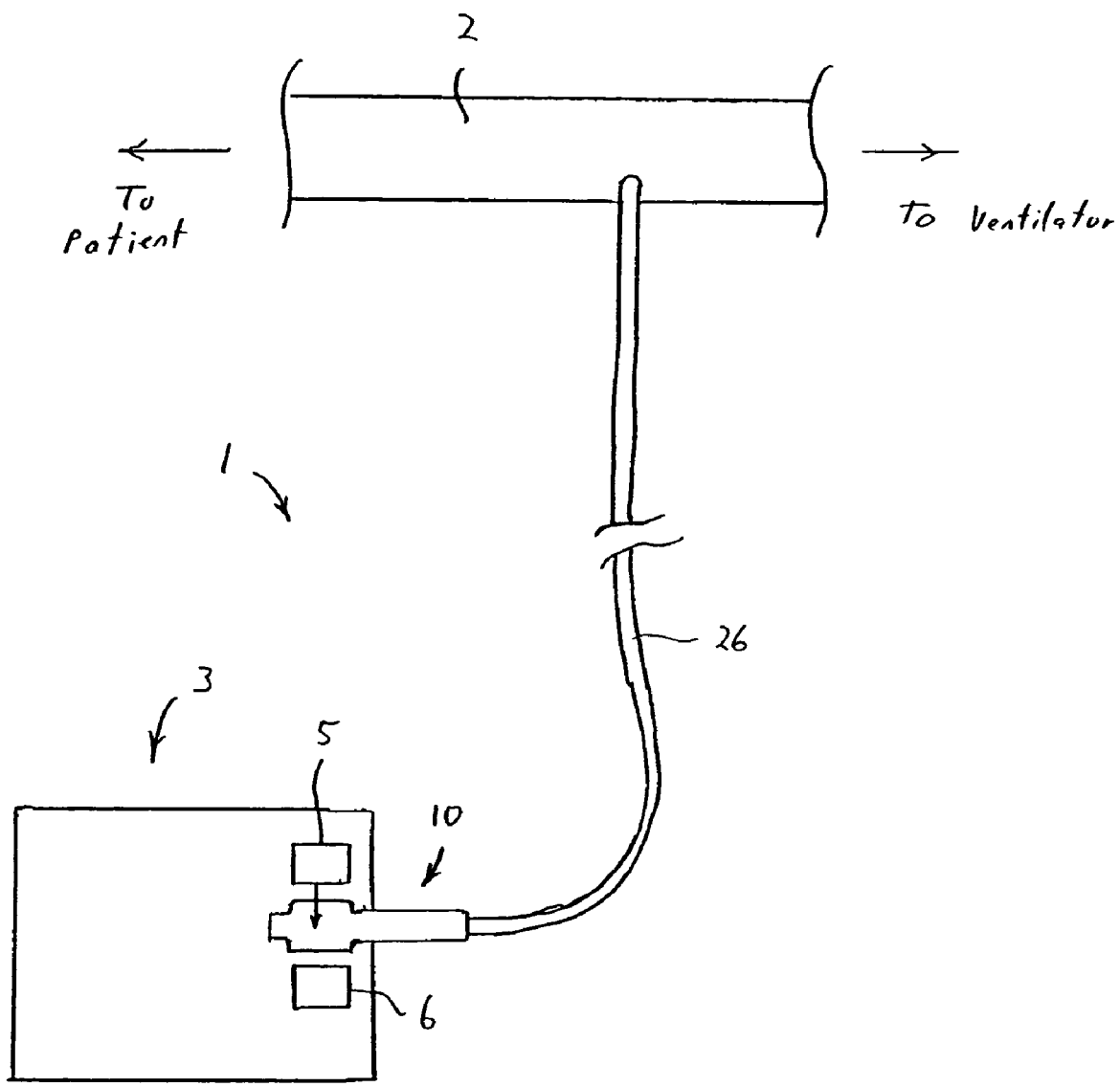
FIG. 1 is a schematic diagram of a gas monitoring system including a gas sampling assembly according to the principles of the present invention.

Referring to the drawings in general and initially to FIG. 1, in particular, an exemplary embodiment side stream gas monitoring system 1 including a filter assembly 10 according to the present invention is illustrated. Gas monitoring system includes a sampling line 26 that is coupled to a patient circuit 2, which is, in turn, in connected to an airway of patient (not shown) so that a portion of the gas in the patient circuit is diverted into sampling line 26. In the illustrated embodiment, sampling line is shown connected to patient circuit 2, which is typically accomplished using an airway adapter. It is to be understood, however, that sampling line 26 can be connected to the patient's airway in any conventional manner, such as through a nasal cannula.

Filter assembly 10 is coupled to an end of the sample line distal from the patient circuit and proximate to a gas monitoring system, generally indicated at 3. The present invention contemplates that gas monitoring system 3 is any conventional sidestream gas monitoring system, which typically includes a radiation emitter 5 and receiver 6 to detect the gas constituents within a sample cell placed in optical alignment with the emitter and receive using well know radiation absorption techniques.

Figure 2:
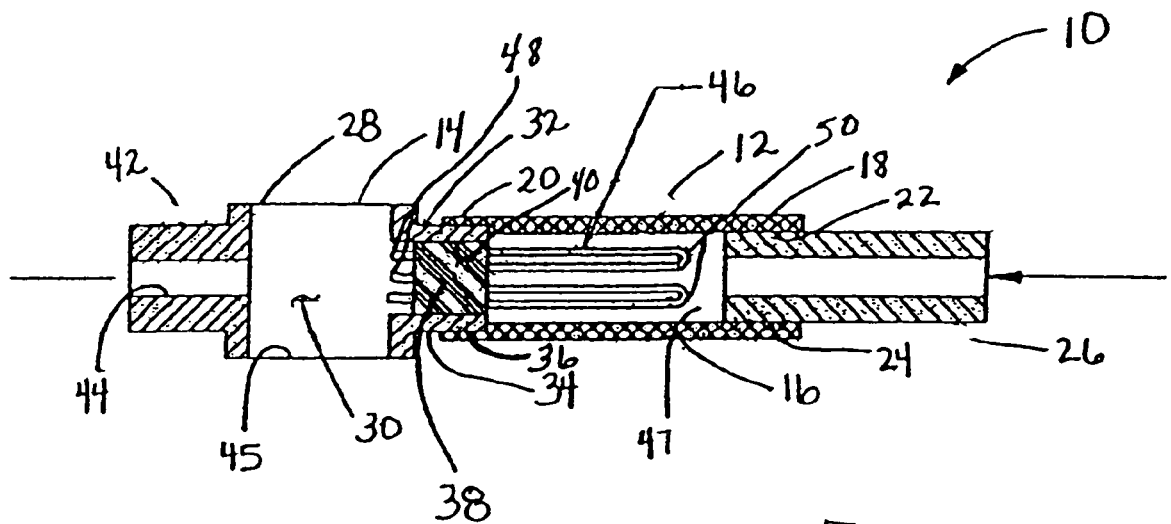
FIG. 2 is a cross-sectional view of a first embodiment of a gas sampling assembly according to the principles of the present invention.

Referring now to FIGS. 1 and 2, a first exemplary embodiment of a gas sampling assembly 10 according to the principles of the present invention will be discussed. Gas sampling assembly 10 includes a filter portion 12 and a sample collection portion 14. Filter portion 12 includes a housing 16 typically formed of a suitable polymer, such as PVC, having a first upstream end 18 and a second downstream end 20. In this embodiment, housing 16 is cylindrical in shape. However, the present invention contemplates that housing 16 can have any suitable shape or length.

First upstream end 18 of housing 16 includes an inner perimeter defined by an inner wall 22. Inner wall 22 is configured to be coupled to an outer wall 24 of a gas sampling line 26 through which an expired gas sample to be monitored may be received. Outer wall 24 of the gas sampling line 26 defines a perimeter that substantially approximates the inner perimeter defined by inner wall 22 such that outer wall 24 of gas sampling line 26 and inner wall 22 are coupled to one another in a fluid-tight and gas-tight manner. Such fluid-tight and gas-tight coupling mechanisms are known to those of ordinary skill in the art and, accordingly, will not be discussed further herein.

Sample collection portion 14 includes a main body section 28, a portion of the internal volume of which forms a sample chamber 30 in which the filtered, expired gases is collected for measurements to be taken thereof, as more fully described below. It is currently preferred that sample collection portion 14 is formed of polycarbonate. Sample collection portion 14 further includes a first side portion 32, a portion of an outer surface 34 of that is coupled with second downstream end 20 of filter portion 12 in a fluid-tight and gas-tight manner. Similar to the coupling of outer wall 24 of gas sampling line 26 to inner wall 22 of first upstream end 18 of housing 16, outer surface 34 of first side portion 32 defines a perimeter that substantially approximates the inner perimeter of second downstream end 20 of housing 16, such inner perimeter of second downstream end 20 being defined by an inner wall 36 thereof. Accordingly, outer surface 34 and inner wall 36 are coupled by a fluid-tight and gas-tight arrangement, as known to those skilled in the art.

As illustrated in FIG. 2, the inner perimeter of second downstream end 20 of housing 16 is greater than the inner perimeter of first upstream end 18. It will be understood and appreciated by those skilled in the art, however, that, in addition to the illustrated relation, the respective inner perimeters of first and second ends 18, 20 may approximate one another, or the inner perimeter of first upstream end 18 may exceed that of second downstream end 20. Such relation of inner perimeters depends upon the desired application and such variations are contemplated to be within the scope hereof.

Disposed within an upstream region of first side portion 32 of sample collection portion 14 is a termination block 38. Termination block 38 extends across the inner perimeter of first side portion 32, the inner perimeter being defined by an inner surface 40 of first side portion 32, such that a fluid-tight and gas-tight seal is created.

Sample collection portion 14 further includes a second side portion 42, substantially longitudinally aligned with first side portion 32. Second side portion 42 includes an inner perimeter, defined by an inner surface 44 thereof, which is of a dimension less than the inner perimeter of sample chamber 30, the inner perimeter of sample chamber 30 being defined by an inner wall 45 thereof. In use, expired, filtered gases, once collected in sample chamber 30, pass through second side portion 42 and are exhausted from sample chamber 30.

Disposed within a fiber chamber 47 of housing 16 is one or more hydrophobic fiber elements 46. Fiber elements 46 are, in the currently preferred embodiment, formed of a hydrophobic filter media having a pore size of less than or equal to 5 microns. One suitable example is polypropylene. In a further preferred embodiment, fiber elements 46 are hollow. In the illustrated embodiment, fiber elements 46 are folded back on themselves to form loops such that all open ends 48 thereof are located proximate second downstream end 20 of housing 16 and looped ends 50 are located in proximity to first upstream end 18 of housing 16. In addition, fiber elements 46 are disposed in housing 16 such that a length-wise axis of the fibers is substantially aligned with a length-wise axis of the housing.

In the illustrated embodiment, the downstream portions of fiber elements 46, proximate open ends 48 thereof, are embedded in termination block 38 such that the open ends of the fiber elements extend beyond the termination block and into sample chamber 30. In this manner, gases are communicated from fiber chamber 47 of housing 16 directly to the sample chamber only through the fiber elements, as more fully described below.

It will be understood and appreciated by those skilled in the art that rather than being folded back on themselves to form loops as shown in FIG. 2, the hollow fiber elements may include a closed sealed end, such closed sealed end being positioned proximate first upstream end 18 of housing 16. In this manner, communication of gases from fiber chamber 47 of housing 16 to sample chamber 30 is still accomplished only through fiber elements 46, as more fully described below. Such alternative is contemplated to be within the scope hereof.

Figure 3:
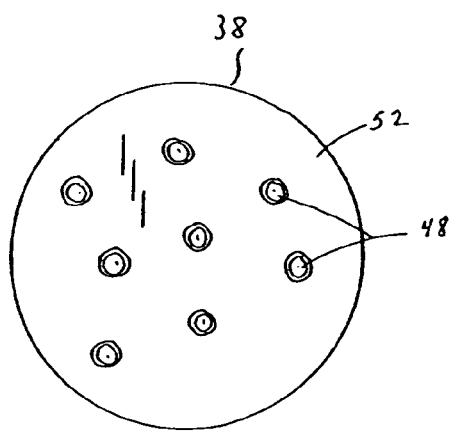
FIG. 3 is a side view of a first embodiment for the outlet of the filter portion of the gas sampling assembly of FIG. 2.

FIG. 3 illustrates an outlet 52 of housing 16 disposed at the downstream end of termination block 38. More specifically, FIG. 3 illustrates a downstream end of termination block 38 and the arrangement of the outlet of the fiber elements 46. As is apparent, the bores or open ends 48 of fiber elements 46 are arranged in a substantially evenly spaced arrangement within the perimeter of outlet 52. In this configuration, outlet 52 of filter portion 12 optimally fills and flushes the interior volume of sample chamber 30 with the filtered gases, as more fully described below.

In operation, a patient expires gases containing liquids such as water, blood, mucus, medications and the like, into a nasal cannula (not shown), gas mask (not shown) or the like. Downstream of the nasal cannula (or other such respiratory collection mechanism), the expired gases leave the mainstream conduit and enter gas sampling line 26 such that at least a portion of the gases are directed toward sidestream gas sampling assembly 10. Gas sampling line 26 forms a conduit through which the expired gases enters filter portion 12 of gas sampling assembly 10. Upon entering filter portion 12, the gases still contain liquids such as water, blood, mucus, medications and the like, which are desirably substantially filtered from the gases prior to the gases being directed toward sample chamber 30.

As the expired gases enter filter portion 12, they encounter the looped ends 50 (or closed sealed ends) of fiber elements 46. Because fiber elements 46 are formed of a hydrophobic material, such as polypropylene, gases are permitted to pass therethrough but the passage of liquids is substantially prevented. Thus, gases substantially free of liquid condensate are permitted to pass only through fiber elements 46, while any liquids present in the expired gases are substantially prevented from entering or passing into the interior of the fiber elements.

Because termination block 38 forms a gas-tight and fluid-tight seal across the inner perimeter of the first side portion of the sample collection portion 14, and a fluid-tight and gas-tight seal is also formed between outer surface 34 of first side portion 32 of sample collection portion 14 and inner wall 36 of second downstream end 20 of filter portion 12, the only way substances may be communicated from fiber chamber 47 of housing 16 to sample chamber 30 is through fiber elements 46. Accordingly, gases substantially free of liquid condensate are permitted to pass through the fiber elements and directly into the sample chamber, while any liquids present in the expired gases are substantially prevented from leaving filter portion 12 of gas sampling assembly 10. Liquids, instead, collect within fiber chamber 47 of housing 16.

The gases free of liquid condensate pass through fiber elements 46, through open ends 48 disposed at outlet 52 and into sample chamber 30 where measurements may be taken thereof, e.g., using optical sensing techniques and the like. Because open ends 48 of fiber elements 46 are in a substantially evenly spaced arrangement within the perimeter of outlet 52, gases enter sample chamber 30 in a substantially uniform manner. In this way, there is prevented an accumulation of gases in one area or another of sample chamber 30 and more consistent and accurate measurements may be taken. The substantially liquid-free gas is exhausted from sample chamber 30 through a conduit formed by inner surface 44 of second side portion 42. The substantially evenly spaced arrangement of open ends 48 of hollow fiber elements 46 within the perimeter of outlet 52 permits the filtered gases within sample chamber 30 to be substantially uniformly flushed from the sample chamber and into the conduit formed by inner surface 44 of second side portion 42.

In this manner, liquids are substantially prevented from reaching sample chamber 30 and, accordingly, measurements taken of the gases in the sample chamber are less likely to be distorted due to moisture in the gas sample. Further, due to the disposition of open ends 48 of fiber elements 46 directly into sample chamber 30, the waveform of the exhaled gas sample is permitted to proceed substantially undisturbed or undegraded from the point at which the sample is collected to the point at which measurements are taken. That is, it can be appreciated from the forgoing description that the present invention provides a gas sampling assembly that does not substantially disturb or degrade the waveform of expired gases. Furthermore, the gas sampling assembly is integrated with a filter for separating undesired liquid condensate and other contaminants from respiratory gases to be monitored.

Figure 4:
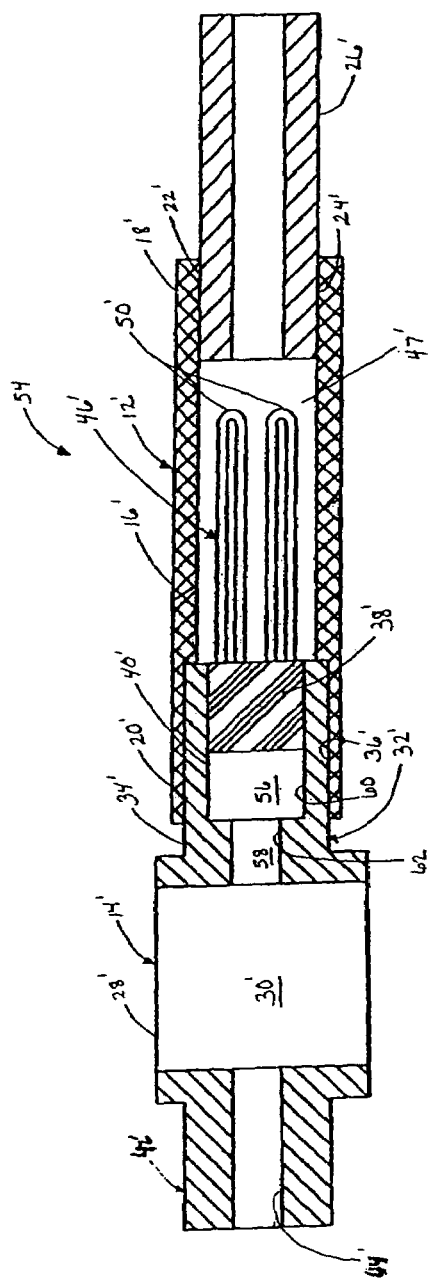
FIG. 4 is a cross-sectional view of a second embodiment of a gas sampling assembly of the present invention.

Referring now to FIG. 4, a second embodiment of a gas sampling assembly of the present invention is illustrated and denoted generally by reference numeral 54. Like gas sampling assembly 10 of FIG. 2, gas sampling assembly 54 includes a filter portion 12' and a sample collection portion 14'. Filter portion 12' includes a housing 16', typically formed of a suitable polymer such as PVC, having a first upstream end 18' end and a second end 20'. First upstream end 18' of housing 16' includes an inner perimeter defined by an inner wall 22' that is configured to be coupled to an outer wall 24' of a gas sampling line 26' through which an expired gas sample to be monitored may be received. Outer wall 24' and inner wall 22' are coupled to one another in a fluid-tight and gas-tight manner.

Sample collection portion 14' of gas sampling assembly 54 includes a main body section 28', a portion of the internal volume of which forms a sample chamber 30' in which the filtered, expired gases is collected for measurements to be taken thereof. It is currently preferred that main body section 28' is formed of polycarbonate. Sample collection portion 14' further includes a first side portion 32', a portion of an outer surface 34' of which is coupled with second downstream end 20' of filter portion 12' in a fluid-tight and gas-tight manner. Similar to the coupling of outer wall 24' of gas sampling line 26' to inner wall 22' to first upstream end 18' of housing 16', outer surface 34' of first side portion 32' defines a perimeter that substantially approximates the inner perimeter of second downstream end 20' of housing 16', such inner perimeter being defined by an inner wall 36' thereof. Accordingly, outer surface 34' of first side portion 32' and inner wall 36' of second downstream end 20' of housing 16' are coupled by a fluid-tight and gas-tight arrangement.

Again, it will be understood and appreciated by those of ordinary skill in the art that the inner perimeter of first upstream end 18' may be less than the inner perimeter of second downstream end 20', as shown, the respective inner perimeters may approximate one another, or the inner perimeter of first upstream end 18' may be greater than the inner perimeter of second downstream end 20'. Such relation of inner perimeters depends upon the desired application and all variations are contemplated to be within the scope of the present invention.

Disposed within a portion of first side portion 32' of sample collection portion 14' is a termination block 38' that extends across the inner perimeter of a portion of first side portion 32', the inner perimeter being defined by an inner surface 40' of first side portion 32'. In this manner, a fluid-tight and gas-tight seal is created at the termination block.

Also, disposed within an upstream region of first side portion 32' of main body section 28', are a gas sample collection chamber 56 and a conduit 58. Gas sample collection chamber 56 is positioned downstream from termination block 38' and conduit 58 is positioned downstream of gas sample collection chamber 56. Gas sample collection chamber 56 has a perimeter, defined by an inner surface 60 thereof, which substantially approximates the perimeter of termination block 38', and conduit 58 has a perimeter, defined by an inner surface 62 thereof, which is smaller than the inner perimeter of gas sample collection chamber 56. In this manner, filtered gases are communicated from a fiber chamber 47' of housing 16' into gas sample collection chamber 56, and then into conduit 58, and subsequently into sample chamber 30'. Such operation is more fully described below.

Sample collection portion 14' further includes a second side portion 42', axially aligned with first side portion 32'. Second side portion 42' includes an inner perimeter defined by an inner surface 44' thereof that substantially approximates the inner perimeter of conduit 58, the inner perimeter of conduit 58 being defined by the inner surface 62 thereof. Expired, filtered gases, once collected in sample chamber 30', passes through second side portion 42' and are exhausted from the sample chamber as described above with reference to the embodiment of FIG. 2.

As with the embodiment of FIG. 2, disposed within fiber chamber 47' of housing 16' is one or more substantially axially oriented hydrophobic hollow fiber elements 46'. Hydrophobic fiber elements 46' are, in the currently preferred embodiment, formed of a hydrophobic filter media having a pore size of less than or equal to 5 microns. One suitable example is polypropylene. Hydrophobic fiber elements 46' are folded back on themselves to form loops such that all of the open ends (not shown) thereof are located near second downstream end 20' of housing 16', and looped ends 50' are located near first upstream end 18' of the housing. The downstream portions of fiber elements 46', proximate the open ends 48' thereof, are embedded in the termination block 38'. In this embodiment, open ends 48' of fiber elements 46' terminate coextensively with the downstream end of termination block 38'. It is to be understood, however, that the open ends of the fiber elements may extend beyond the termination block and into gas sample collection chamber 56. In this manner, gases are communicated from fiber chamber 47' of housing 16' into gas sample collection chamber 56 only through fiber elements 46'.

It will again be understood and appreciated by those of ordinary skill in the art that rather than being folded back on themselves to form loops as shown in FIG. 4, fiber elements 46' may include a closed sealed end, such closed sealed end being positioned proximate first upstream end 18' of housing 16'.

In operation, a patient's expired gases enter the gas sampling line 26' and filter portion 12' of the gas sampling assembly 54 as described above with reference to FIGS. 1 and 2. As the expired gases enters filter portion 12' gas sampling assembly 54, the gases encounter looped ends 50' of fiber elements 46'. Fiber elements 46' are formed of a hydrophobic material such that gases are permitted to pass therethrough but the passage of liquids is substantially prevented. Thus, gases substantially free of liquid condensate are permitted to pass only through fiber elements 46' and into gas sample collection chamber 56, where they are initially collected prior to being directed toward sample chamber 30'. The gases are then directed from gas sample collection chamber 56 into conduit 58 and, subsequently, into sample chamber 30', where measurements may be taken thereof, e.g., using optical sensing techniques and the like. The substantially liquid-free gas is exhausted from sample chamber 30' as described above with reference to FIGS. 1 and 2.

With the embodiment of FIG. 4, similar to that of FIG. 2, liquids are substantially prevented from reaching sample chamber 30' and, accordingly, measurements taken of the gases in sample chamber 30' are less likely to be distorted due to moisture in the gas sample. Further, due to the relatively small distance between filter portion 12' and sample chamber 30', the waveform of the exhaled gas sample is permitted to proceed substantially undisturbed from the point at which the sample is collected to the point at which the measurements are taken. As a result, the waveform indicative of the level of monitored gas in the sample cell is not substantially degraded, as can be the case in conventional systems, where the filter element is located a relatively long distance from the sample cell where the constituent levels are measured and connected with a relatively long hose or conduit.

Figure 5:
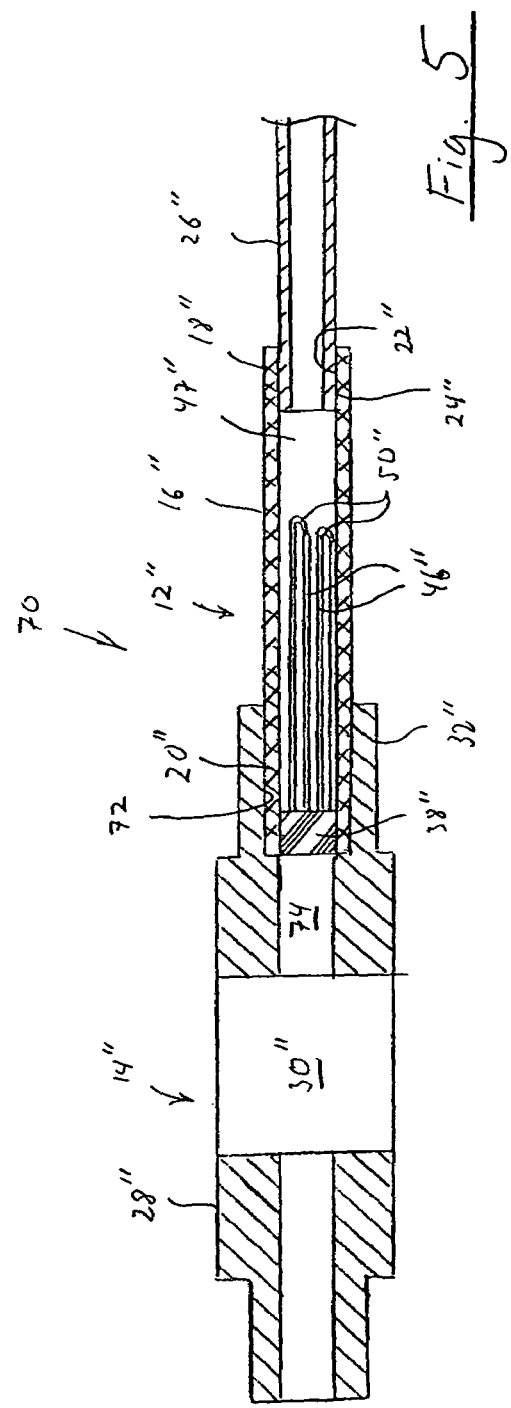
FIG. 5 is a cross-sectional view of a third embodiment of a gas sampling assembly of the present invention.

Referring now to FIG. 5, a third embodiment of a gas sampling assembly of the present invention is illustrated and denoted generally by reference numeral 70. Like gas sampling assembly 10 of FIG. 2, gas sampling assembly 70 includes a filter portion 12" and a sample collection portion 14". Filter portion 12" includes a housing 16", typically formed of a suitable polymer such as PVC, having a first upstream end 18" end and a second end 20". First upstream end 18" includes an inner perimeter defined by an inner wall 22" that is configured to be coupled to an outer wall 24" of a gas sampling line 26" through which an expired gas sample to be monitored may be received. Outer wall 24" and inner wall 22" are coupled to one another in a fluid-tight and gas-tight manner.

Sample collection portion 14" includes a main body section 28", a portion of the internal volume of which forms a sample chamber 30" in which the filtered, expired gases is collected for measurements to be taken thereof. It is currently preferred that main body section 28" is formed of polycarbonate. Sample collection portion 14" further includes a first side portion 32", a portion of an inner surface 72 of which is coupled with second downstream end 20" of housing 16" in a fluid-tight and gas-tight manner. Similar to the coupling of outer wall 24" of gas sampling line 26" to inner wall 22" to first upstream end 18" of housing 16", inner surface 72 of first side portion 32" defines a perimeter that substantially approximates an outer perimeter of second downstream end 20" of housing 16". Accordingly, inner surface 72 of first side portion 32" and an outer wall of second downstream end 20" of housing 16" are coupled in a fluid-tight and gas-tight arrangement.

Again, it will be understood and appreciated by those of ordinary skill in the art that the inner perimeter of first upstream end 18" may be less than the inner perimeter of second downstream end 20", as shown, the respective inner perimeters may approximate one another, or the inner perimeter of first upstream end 18" may be greater than the inner perimeter of second downstream end 20". Such relation of inner perimeters depends upon the desired application and all variations are contemplated to be within the scope of the present invention.

In the embodiment illustrated in FIG. 5, termination block 38" is disposed in second downstream end 20" of housing 16" so that a fluid-tight and gas-tight seal is created at the termination block. A conduit 74 is defined within an upstream region of first side portion 32" of main body section 28" to communicate gas existing a downstream end of termination block 38" with sample chamber 30". In the illustrated exemplary embodiment, a diameter of conduit 74 is substantially the same as an inside diameter of downstream second end 20" of housing 16", which corresponds to an inside diameter of fiber chamber 47". Providing matching diameters between fiber chamber 47" and conduit 74" helps to reduce disturbances or turbulence in the flow gas passing through the gas sampling assembly.

As with the embodiment of FIGS. 2 and 4, disposed within fiber chamber 47" of housing 16" is one or more substantially axially oriented hydrophobic hollow fiber elements 46". Hydrophobic fiber elements 46" are, in the currently preferred embodiment, formed of a hydrophobic filter media having a pore size of less than or equal to 5 microns. One suitable example is polypropylene. Hydrophobic fiber elements 46" are folded back on themselves to form loops such that all of the open ends (not shown) thereof are located near second downstream end 20" of housing 16", and looped ends 50" are located near first upstream end 18" of the housing. The downstream portions of fiber elements 46" are embedded in the termination block 38".

In this embodiment, the downstream ends of fiber elements 46" terminate coextensively with the downstream end of termination block 38" or within the termination block so that they do not extend beyond the surface of the termination block. It is to be understood, however, that the open ends of the fiber elements may extend beyond the termination block and into conduit 74. In this manner, gases are communicated from fiber chamber 47" of housing 16" via fiber elements 46" into conduit 74, and then into sample chamber 30".

It will again be understood and appreciated by those skilled in the art that rather than being folded back on themselves to form loops as shown in FIG. 5, fiber elements 46" may include a closed sealed end, such closed sealed end being positioned proximate first upstream end 18" of housing 16".

The operation of gas sampling assembly 70 is similar to that described above with reference to FIGS. 1–4. Thus, a detailed explanation is omitted for the sake of brevity. With the embodiment of FIG. 5, similar to that of FIGS. 2 and 4, liquids are substantially prevented from reaching sample chamber 30" and, accordingly, measurements taken of the gases in sample chamber 30" are less likely to be distorted due to moisture in the gas sample. Further, due to the relatively small distance between filter portion 12" and sample chamber 30", the waveform of the exhaled gas sample is permitted to proceed substantially undisturbed from the point at which the sample is collected to the point at which the measurements are taken.

It will be understood and appreciated by those skilled in the art that in each of the embodiments of FIGS. 1–5, the various portions of the gas sampling assemblies (e.g., the filter portions, the sample collection portions, etc.) may be formed as separate components or may be integrally formed. For example, the present invention contemplates forming sample collection portion 14" and filter portion 12" of FIG. 5 as separate structures that are assembled during manufacture to form a unitary assembly for the gas sampling assembly. Further, it will be understood that the termination block, the sample chamber, the arrangement of the fiber elements and the termination block, and the conduits associated with the termination block and/or sample chamber can have any one of a variety of configurations. Such variations are contemplated to be within the scope of the present invention and the present invention is not intended to be limited to the specific structures illustrated. In addition, other elements, such as optical filters and windows can be provided in association with the sample chamber without departing from the spirit and scope of this invention.

Figure 6:
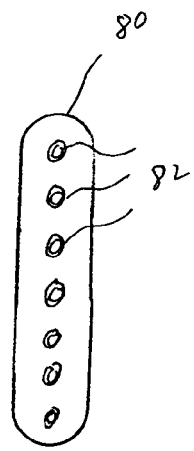
FIG. 6 is a side view of a second embodiment for the outlet of the filter portion of the gas sampling assembly.

For example, FIG. 6 illustrates a second embodiment for a termination block 80 and shows a further configuration for the open ends 82 of the fiber elements coupled thereto. That is FIG. 6 is similar to FIG. 3, except that it shows an alternative configuration for the termination block and fiber elements. In the embodiment of FIG. 6, termination block 80 has a relatively rectangular configuration and the open ends of the fiber elements are disposed in a linear array. Preferably, the linear array is aligned relatively to the sample chamber such that the open ends of the fiber elements are disposed in a plane that is generally perpendicular to the direction in which radiation is passed through the sample chamber. This arrangement in that it presents a uniform wall of gas directly into the sample chamber for measurement by the gas monitoring system.

Figure 7:
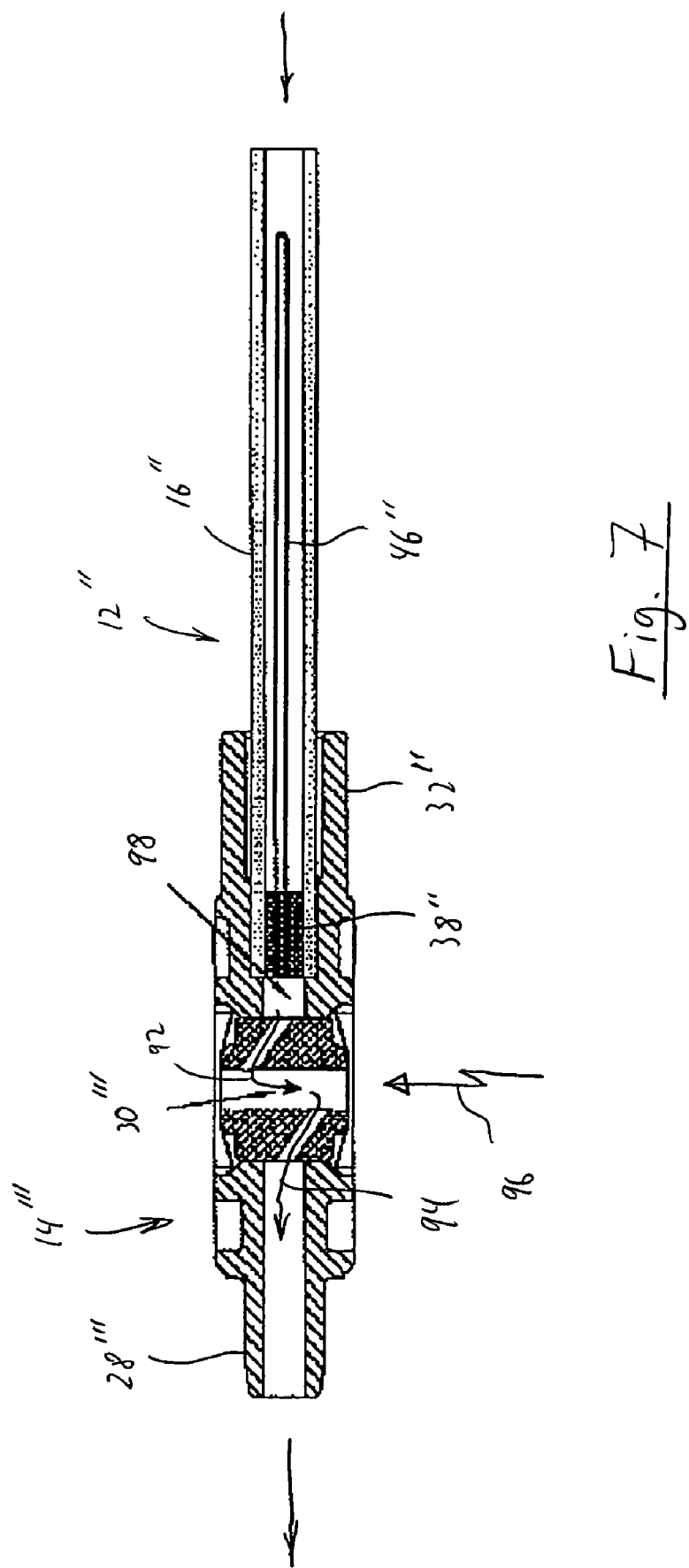
FIG. 7 is a cross-sectional view of a third embodiment of a gas sampling assembly according to a further embodiment of the present invention.

FIG. 7 illustrates a gas sampling assembly 90 that is similar to that shown in FIG. 5, including a filter portion 12" and a sample collection portion 14'''. In this embodiment, unlike that of FIG. 5, the passage in main body section 28''' includes a "Z" shaped path through a sample chamber 30"', as indicated by arrows 92 and 94. Sample chamber 30 includes open ends with a window disposed at each open end so that irradiation 96 can be passed through the sample chamber. An inlet portion 98 of the passage communicates the outlet of filter portion 12" with the sample chamber. This "Z" shaped configuration for the optical sampling portion of the sample collection portion is described in co-pending U.S. patent application No. 60/416,875, the contents of which are incorporated herein by reference. It is to be understood that other configurations for the sample collection portion and the passage therethrough are contemplated by the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A gas sampling assembly comprising:
    a filter portion including a housing having an upstream first end, a downstream second end, and a gas flow path defined through the housing from the first end to the second end;
    a sample collection portion including a body section having a sample chamber defined therein, wherein the body section is coupled to the downstream second end of the housing such that the housing and the body section define a unitary assembly with the sample chamber being in fluid communication with the gas flow path in the housing, and wherein the body section includes an energy transmissive portion such that a constituent of a gas in the sample chamber is adapted to be monitored through the energy transmission portion; and
    at least one filter element disposed in the housing.

2. The gas sampling assembly of claim 1, wherein the filter element includes an upstream closed end and a downstream open end, and wherein the upstream closed end of the filter element is a looped end formed by the filter element being folded back on itself.

3. The gas sampling assembly of claim 1, further comprising a gas sampling line coupled to the upstream first end of the housing.

4. The gas sampling assembly of claim 3, further comprising a conduit in fluid communication with the sample chamber to permit communication of gases out of the sample chamber.

5. The gas sampling assembly of claim 1, wherein the housing and body section are integrally formed from a unitary material.

6. The gas sampling assembly of claim 1, wherein the body section includes:
    a gas sample collection chamber defined in the body section upstream of the sample chamber, the gas sample collection portion configured to collect filtered gases therein; and
    a conduit defined in the body section upstream of the sample chamber and downstream of the gas sample collection chamber, the conduit communicating the gas sample collection chamber with the sample chamber.

7. The gas sampling assembly of claim 1, wherein the at least one filter element is a hydrophobic fiber element.

8. The gas sampling assembly of claim 1, further comprising a termination block positioned in the body section of the sample chamber so as to form a seal across an upstream end region of the sample collection portion, wherein the at least one filter element is coupled to the termination block.

9. The gas sampling assembly of claim 8, wherein at least one of the filter element is coupled to the termination block such that the downstream open end protrudes from a surface of the termination block in a direction toward the sample chamber.

10. The gas sampling assembly of claim 8, wherein all of the filter elements are coupled to the termination block such that the downstream open ends do not protrude from a surface of the termination block.

11. The gas sampling assembly of claim 8, wherein the at least one filter element includes an upstream closed end and a downstream open end, and wherein the housing includes a filter chamber defined therein in which at least the upstream closed ends of the filter elements are located, wherein the body section includes a conduit communicating the sample chamber with a downstream end of the termination block, and wherein a diameter of the filter chamber and a diameter of the conduit are substantially the same.

12. The gas sampling assembly of claim 8, wherein the at least one filter element includes an upstream closed end and a downstream open end, and wherein a plurality of the filter elements are coupled to the termination block such that the downstream open ends of the plurality of filter elements are disposed in a linear array.

13. A sidestream gas monitoring system comprising:
(a) a sampling line having a first end and a second end for carrying a flow of gas from a patient circuit;
(b) a gas sampling assembly comprising:
(1) a filter portion including a housing having an upstream first end, a downstream second end, and a gas flow path defined through the housing from the first end to the second end, and wherein the upstream first end is connected to the second end of the sampling line,
(2) a sample collection portion including a body section having a sample chamber defined therein, wherein the body section is coupled to the downstream second end of the housing such that the housing and the body section define a unitary assembly, and wherein the sample chamber is in fluid communication with the gas flow path in the housing, and
(4) at least one filter element operatively disposed in the housing; and
(c) a detecting system adapted to measure a constituent of gas contained within the sample chamber.

14. The system of claim 13, wherein the at least one filter element includes an upstream closed end and a downstream open end, and wherein the upstream closed end of the filter element is a looped end formed by the filter element being folded back on itself.

15. The system of claim 13, further comprising a conduit in fluid communication with the sample chamber to permit communication of gases out of the sample chamber.

16. The system of claim 13, wherein the housing and body section are integrally formed from a unitary material.

17. The system of claim 13, wherein the at least one filter elements is a hydrophobic material.

18. The system of claim 13, further comprising a termination block positioned in the body section of the sample chamber so as to form a seal across an upstream end region of the sample collection portion, wherein the at least one filter element is coupled to the termination block.

19. The system of claim 18, wherein the body section includes:
a gas sample collection chamber defined in the body section upstream of the sample chamber and downstream of the termination block, the gas sample collection portion configured to collect filtered gases therein; and
a conduit defined in the body section upstream of the sample chamber and downstream of the gas sample collection chamber, the conduit communicating the gas sample collection chamber with the sample chamber.

20. The system of claim 18, wherein the at least one filter element includes an upstream closed end and a downstream open end, and wherein at least one of the filter elements is coupled to the termination block such that the downstream open end protrudes from a surface of the termination block in a direction toward the sample chamber.

21. The system of claim 18, wherein the at least one filter element includes an upstream closed end and a downstream open end, and wherein all of the filter elements are coupled to the termination block such that the downstream open ends do not protrude from a surface of the termination block.

22. The system of claim 18, wherein the at least one filter element includes an upstream closed end and a downstream open end, wherein the housing includes a filter chamber defined therein in which at least the upstream closed ends of the at least one filter element is located, wherein the body section includes a conduit communicating the sample chamber with a downstream end of the termination block, and wherein a diameter of the filter chamber and a diameter of the conduit are substantially the same.

23. The system of claim 18, wherein the at least one filter element includes an upstream closed end and a downstream open end, and wherein a plurality of filter elements are coupled to the termination block such that the downstream open ends of the plurality of filter elements are disposed in a linear array.

* * * * *